United States Patent
Zhu et al.

(10) Patent No.: US 11,510,654 B2
(45) Date of Patent: Nov. 29, 2022

(54) ULTRASONIC SYSTEM OF CONTACT TYPE FLEXIBLE CONFORMAL ULTRASONIC PROBE AND METHOD FOR THE SAME

(71) Applicant: SHANGHAI SOUNDWISE TECHNOLOGY CO., LTD., Shanghai (CN)

(72) Inventors: Ruixing Zhu, Shanghai (CN); Xuebing Chen, Shanghai (CN); Jianqiao Zhou, Shanghai (CN); Zhenhua Liu, Shanghai (CN); Lei Chen, Shanghai (CN)

( * ) Notice: Subject to any disclaimer, the term of this patent is extended or adjusted under 35 U.S.C. 154(b) by 0 days.

(21) Appl. No.: 17/222,649

(22) Filed: Apr. 5, 2021

(65) Prior Publication Data

US 2021/0315544 A1 Oct. 14, 2021

(30) Foreign Application Priority Data

Apr. 9, 2020 (CN) .......................... 202010272050.0

(51) Int. Cl.
*A61B 8/00* (2006.01)
*A61B 8/08* (2006.01)

(52) U.S. Cl.
CPC .......... *A61B 8/5207* (2013.01); *A61B 8/4254* (2013.01); *A61B 2562/066* (2013.01)

(58) Field of Classification Search
CPC ................ A61B 8/5207; A61B 8/4254; A61B 2562/066; A61B 8/4444; G01S 7/52079
See application file for complete search history.

(56) References Cited

U.S. PATENT DOCUMENTS

| | | | | |
|---|---|---|---|---|
| 6,153,463 | A * | 11/2000 | Wei | H01L 28/40 438/253 |
| 9,746,448 | B2 * | 8/2017 | Gu | G01N 29/24 |
| 10,426,435 | B2 * | 10/2019 | Chiang | G01S 15/8925 |
| 10,602,989 | B2 * | 3/2020 | Wang | A61B 1/00172 |
| 2003/0028107 | A1 * | 2/2003 | Miller | A61B 5/6819 600/437 |
| 2004/0002652 | A1 * | 1/2004 | Phelps | A61B 8/483 600/437 |
| 2013/0128702 | A1 * | 5/2013 | Degertekin | G01S 15/8927 367/140 |
| 2016/0045184 | A1 * | 2/2016 | Courtney | A61B 8/5207 600/424 |
| 2019/0150895 | A1 * | 5/2019 | Tian | A61B 8/4254 |

* cited by examiner

*Primary Examiner* — Serkan Akar
*Assistant Examiner* — Gabriel Victor Popescu
(74) *Attorney, Agent, or Firm* — Clement Cheng

(57) ABSTRACT

The invention relates to the field of ultrasonic imaging detection, and more particularly, to an ultrasonic system of a contact type flexible conformal ultrasonic probe and a method for the same. The ultrasonic system comprises: a flexible probe, comprising a flexible detection surface, a plurality of probe units, and a soft film sensing surface; a switch module; a control module, comprising: a transmitting control unit for sequentially controlling the probe units in the probe array to transmit the ultrasonic signal; a receiving control unit for sequentially controlling the probe units in the probe array to receive the ultrasonic signal, and for processing the ultrasonic signal to obtain a ultrasonic image. The present invention has the following beneficial effects: the use of a flexible probe for acquiring an ultrasonic image allows to solve the problem that the operation process and imaging steps are complicated when using a rigid probe.

9 Claims, 4 Drawing Sheets

ULTRASONIC SYSTEM OF CONTACT TYPE FLEXIBLE CONFORMAL ULTRASONIC PROBE AND METHOD FOR THE SAME

BACKGROUND OF THE INVENTION

1. Field of the Invention

The invention relates to the field of ultrasonic imaging detection, and more particularly, to an ultrasonic system of a contact type flexible conformal ultrasonic probe and a method for the same.

2. Description of the Related Art

In recent years, ultrasound imaging has played a significant role in research fields, such as disease monitoring. Of note, whether an ultrasound image is acquired in an accurate and convenient way is essential for the diagnosis and treatment of patients.

The ultrasound imaging is carried out by using a rigid probe. However, the transmitting angle of each probe unit in the rigid probe, and relative positions between two of the probe units are fixed. Therefore, in order to transmit ultrasonic signal for ultrasound imaging, an operator is required to pre-set the location, the shape, and the angle of the rigid probe, and they have to control the rigid probe to move around, so as to acquire an accurate ultrasound image. All of those steps make the imaging of the ultrasound image become complicated.

SUMMARY OF THE INVENTION

Given that the foregoing problems exist in the prior art, the present invention provides an ultrasonic system of a contact type flexible conformal ultrasonic probe and a method for the same.

An ultrasonic system of a contact type flexible conformal ultrasonic probe for generating an ultrasonic image, comprising:

a flexible probe, comprising a flexible detection surface, a plurality of probe units, and a soft film sensing surface, wherein the plurality of probe units are configured to transit/receive ultrasonic signal, all of the plurality of probe units form a probe array, the probe array is positioned inside the flexible detection surface, the flexible detection surface is connected to the flexible film sensing surface and changes with deformation of the flexible film sensing surface, the flexible film sensing surface is provided with a capacitive sensor array therein, the capacitive sensor array is configured to detect the deformation of the flexible film sensing surface and to obtain relative deflection angles of each of the plurality of probe units in the probe array;

a switch module, connected to the flexible probe, and configured to sequentially switch a transmitting/receiving state of each of the probe units in the probe array;

a control module, connected to the flexible probe and the switch module, respectively, the control module comprising:

a transmitting control unit for acquiring the relative deflection angles of the plurality of probe units and generating corresponding delay times according to the relative deflection angles, and sequentially controlling the plurality of probe units in the probe array to transmit the ultrasonic signal based on the delay times; and a receiving control unit for sequentially controlling the plurality of probe units in the probe array to receive the ultrasonic signal, and for obtaining the relative deflection angles of the plurality of probe units, and for performing beamforming and image processing on the ultrasonic signal based on the relative deflection angles, so as to obtain the ultrasonic image.

Preferably, the capacitive sensing array comprises:

a plurality of first polar plates;

a plurality of second polar plates, parallel to the plurality of first polar plates;

a plurality of third polar plates, disposed between the plurality of first polar plates and the plurality of second polar plates, and connected to the flexible detection surface, wherein a first capacitance value is set between the plurality of third polar plates and the plurality of first polar plates, a second capacitance value is set between the plurality of third polar plates and the plurality of second polar plates;

a first initial standard value is set correspondingly to the first capacitance value;

a second initial standard value is set correspondingly to the second capacitance value;

a detection element, wherein the detection element is connected to the first polar plate, the second polar plate and the third polar plate, respectively for obtaining a first difference value between the first capacitance value and the first initial standard value, and for obtaining a second difference value between the second capacitance value and the second initial standard value, and for obtaining the relative deflection angle of each of the plurality of probe units in the probe array based on the first difference value and the second difference value.

Preferably, the receiving control unit comprises:

a beamforming element, connected to the flexible probe and the switch module, respectively, configured to obtain the relative deflection angles of the plurality of probe units, configured to control each row of the plurality of probe units in the probe array to sequentially receive the ultrasonic signal through the switch module, and configured to perform beamforming on the ultrasonic signal based on the relative deflection angle and output the ultrasonic signal;

a signal processing element, connected to the beamforming element configured to receive the ultrasonic signal output by the beamforming element, and configured to filter and compress the ultrasonic signal and output the ultrasonic signal; and an image processing element, connected to the signal processing element, configured to receive the ultrasonic signal output by the signal processing element, and configured to perform frame-related processing on the ultrasonic signal to generate the ultrasonic image.

Preferably, wherein the coordinate origin is configured as one probe unit, which has a shortest sound path from the receiving focus thereto, in each row of plurality of probe units in the probe array, the beamforming element is subjected to beamforming process by using the following formula:

$$S_{DAS}(t) = \sum_{i=0, j=0}^{i=n-1, j=m-1} s(t_{(i,j)} - t' - \tau_{(i,j)})$$

wherein $S_{DAS}(t)$ represents the ultrasonic signal which is subjected to the beamforming process;

$s(t_{(i,j)})$ represents the ultrasonic signal received by one of the plurality of the probe units;

i represents the row serial number of the one of the plurality of probe units in the probe array, n represents a number of rows of the plurality of probe units in the probe array;

j represents a column serial number of the one of the plurality of probe units in the probe array, m represents a number of columns of the plurality of probe units in the probe array;

t' represents a transmission time of ultrasonic signal which indicates a shortest distance among distances between all of the plurality of probe units and the receiving focus;

$\tau_{(i,j)}$ represents the delay time of the one of plurality of probe units relative to the coordinate origin.

Preferably, the ultrasonic system of a contact type flexible conformal ultrasonic probe further comprises a client, wherein the client is connected to the receiving control unit for obtaining the ultrasonic image and displaying the ultrasonic image.

An ultrasonic method for a contact type flexible conformal ultrasonic probe, applied to any one of the ultrasonic systems for generating an ultrasonic image, wherein the ultrasonic method comprises the process of a flexible probe transmitting the ultrasonic signal;

the transmitting process comprises:

Step A1, the transmitting control unit controls the plurality of probe units in the probe array to switch to the transmitting state through the switch module;

Step A2, the transmitting control unit obtains the relative deflection angles of the plurality of probe units in the probe array, and generates delay times according to the relative deflection angles; and Step A3, the transmitting control unit controls the plurality of probe units to transmit ultrasonic signal according to the delay times.

Preferably, the ultrasonic method further comprises the process of the flexible probe receiving the ultrasonic signal;

the receiving process comprises:

Step B1, the receiving control unit controls the plurality of probe units in the probe array to switch to the receiving state through the switch module;

Step B2, the receiving control unit obtains the ultrasonic signal received by the probe unit; and Step B3, the receiving control unit obtains the relative deflection angles of the plurality of probe unit in the probe array, and process the ultrasonic signal according to the relative deflection angles, so as to obtain an ultrasonic image.

Preferably, Step B3 further comprises:

Step B31: the beamforming element in the receiving control unit receives the ultrasonic signal, performs beamforming process on the ultrasonic signal based on the relative deflection angle, and outputs the ultrasonic signal;

Step B32: the signal processing element in the receiving control unit receives the ultrasonic signal output by the beamforming element, filters and compresses the ultrasonic signal, and outputs the ultrasonic signal; and Step B33: the image processing element in the receiving control unit receives the ultrasonic signal output by the signal processing element, and performs frame-related processing on the ultrasonic signal to generate the ultrasonic image.

By adopting the above-mentioned technical solutions, the present invention has the following beneficial effects: the use of a flexible probe for acquiring an ultrasonic image allows to solve the problem that the operation process and imaging steps are complicated when using a rigid probe, so that it is easier for relevant operators to carry out the process.

DETAILED DESCRIPTION

The technical solution set forth in the embodiments of the present invention will now be described clearly and fully hereinafter with reference to the accompanying drawings of the embodiments of the present invention. Obviously, such embodiments provided in the present invention are only part of the embodiments instead of all embodiments. It should be understood that all the other embodiments obtained from the embodiments set forth in the present invention by one skilled in the art without any creative work fall within the scope of the present invention.

Notably, the embodiments set forth in the present invention and features of the embodiments may be combined in any suitable manner.

Figure 1:
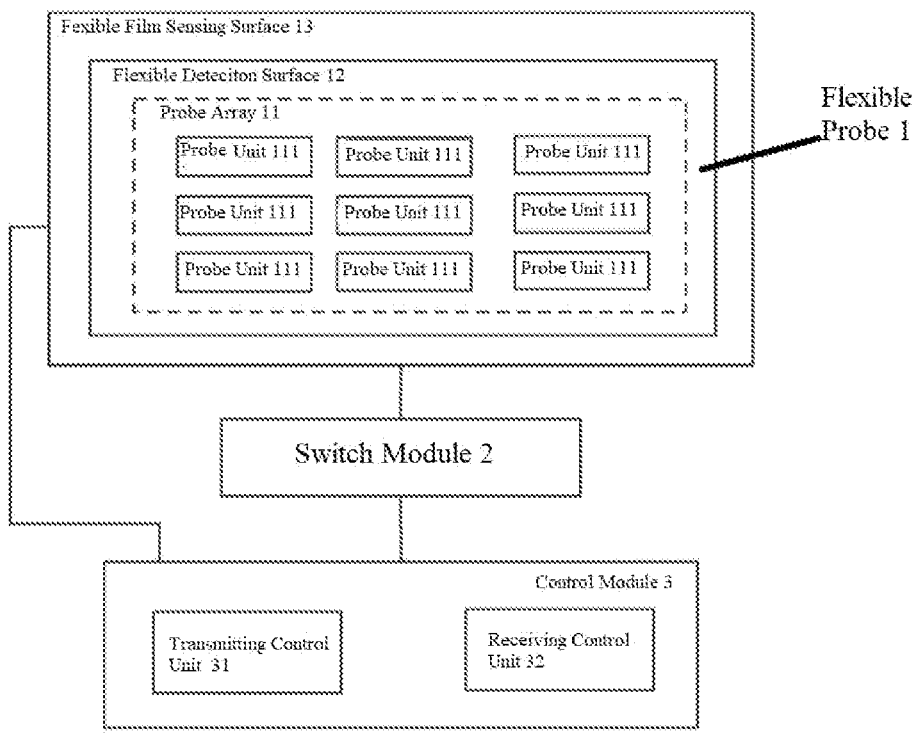
FIG. 1 is a schematic diagram of an overall structure according to a preferred embodiment of the present invention.

The invention provides an ultrasonic system of a contact type flexible conformal ultrasonic probe for generating an ultrasonic image, as shown in FIG. 1, the ultrasonic system comprises:

a flexible probe 1, comprising a flexible detection surface 12, a plurality of probe units 111, and a soft film sensing surface 13, wherein the plurality of probe units 111 are configured to transit/receive an ultrasonic signal, all of the plurality of probe units 111 form a probe array 11, the probe array 11 is positioned inside the flexible detection surface 12, the flexible detection surface 12 is connected to the flexible film sensing surface 13 and changes with deformation of the flexible film sensing surface 13, the flexible film sensing surface 13 is provided with a capacitive sensor array therein, the capacitive sensor array is configured to detect the deformation of the flexible film sensing surface 13 and to obtain relative deflection angles of each of the plurality of probe units 11 in the probe array 11;

a switch module 12, connected to the flexible probe 1, and configured to sequentially switch a transmitting/receiving state of each of the plurality of probe units 111 in the probe array 11;

a control module 3, connected to the flexible probe 1 and the switch module 2, respectively, the control module 3 comprising:

a transmitting control unit 31 for acquiring the relative deflection angles of the plurality of probe unit 111 and generating corresponding delay times according to the relative deflection angles, and sequentially controlling the plurality of probe units 111 in the probe array 11 to transmit the ultrasonic signal based on the delay times; and a receiving control unit 32, for sequentially controlling the plurality of probe units 111 in the probe array 11 to receive the ultrasonic signal, for obtaining the relative deflection angles of the plurality of probe units 111, and for performing beamforming and image processing on the ultrasonic signal based on the relative deflection angles, so as to obtain the ultrasonic image.

Specifically, as described above, in the field of ultrasound imaging detection, the ultrasound image is obtained by using a rigid probe. However, the transmitting angle of each probe unit in the rigid probe, and relative positions between two of the probe units are fixed. Therefore, in order to perform ultrasound imaging by using the rigid probe, the rigid probe remains transmitting ultrasonic signal at a fixed angle, and an operator is required to pre-set the angle of the rigid probe, and the operator has to control the rigid probe to move around, so as to acquire an accurate ultrasound image. It can be seen from the above-mentioned steps that operation steps for carrying out ultrasound imaging by using the rigid probe is quite complicated.

In the prior art, flexible probes are also used for some applications. It is much easier for operators to manipulate the flexible probes than to manipulate the rigid probes. At present, the flexible probes are often used in fields, for example, of the detection of a workpiece on an uneven surface and in A-mode ultrasound detection. A curve of the signal intensity of a detection beam over time or distance can be obtained simply by attaching the flexible probe to a surface to be detected. However, the flexible probes in the prior art cannot be used for ultrasound imaging detection, the key reason is that the ultrasonic signal cannot be focused during the transmitting and receiving process.

In order to solve the above-mentioned defects, the present invention provides an ultrasonic system of a contact type flexible conformal ultrasonic probe, comprising: a flexible probe 1, a switch module 2 and a control module 3, and a flexible detection surface 12, a plurality of probe units 111 and a flexible film sensing surface 13 are provided inside the flexible probe 1, the plurality of probe units 111 form a probe array 11 and are arranged in the flexible detection surface 12. When an operator attaches the flexible probe 1 to the surface of the human body, the flexible detection surface 12 will deform with the flexible film sensing surface 13. The capacitive sensing array located in the flexible film sensing surface 13 can detect the deformation of the flexible film sensing surface 13, so as to obtain a relative deflection angel of each of the probe units 111 in the probe array 11. The control module 3 and the switch module 2 generate the corresponding delay times according to the relative deflection angles of each probe unit 111 to control the transmitting/receiving state of the probe unit 111, to solve the focus problem of the probe unit 111 in the transmitting/receiving process, and finally the function of the flexible probe 1 to acquire ultrasound images is realized.

In particular, the plurality of probe units 111 form a two-dimensional probe array 11. The probe array 11 is disposed inside the flexible detection surface 12, and the flexible detection surface 12 is connected to the flexible film sensing surface 13. In practice, when the operator attaches the flexible probe 1 to the body surface of the patient, the flexible film sensing surface 13 may deform to conform to the contour of the surface of body, and consequently the flexible detection surface 12 may also deform. Finally, each of the probe units 111 can form a different relative deflection angle in the probe array 11.

Accordingly, in order to obtain the relative deflection angle of the probe unit 11, a capacitance sensing array is arranged in the flexible film sensing surface 13. The capacitance sensing array can detect the deformation of the flexible film sensing surface 13, so as to obtain the relative deflection angle of the probe unit 111 in the probe array and to output the relative deflection angle to the switch module 2. The switch module 2 controls a transmitting/receiving state of each probe unit 111 according to the obtained relative deflection angle. Since the probe array 11 in the flexible probe 1 has a plurality of rows and a plurality of columns, the switch module 2 sequentially switches the state of each row of probe units 111 in the probe array 11. After the probe units 111 in one row have completed transmitting and receiving ultrasonic signal, next row of probe units 111 follow to transmit and receive ultrasonic signal.

Furthermore, in order to enable the probe units 111 to focus during the transmitting process, the control module 3 is provided with a transmitting control unit 31 therein, a transmission focus is provided when transmitting the ultrasonic signal. When the flexible probe 1 transmits the ultrasonic signal, the transmitting control unit 31 generates different delay times based on the relative deflection angles of each probe unit 111, so as to control all of the probe units 111 in each group of the probe array 11 to reach a preset focus at exactly the same time.

Furthermore, it is known that the probe unit needs to focus when transmitting the ultrasonic signal, while when receiving the ultrasonic signal, the probe unit 111 also needs to focus, and the only difference lies in that the focus during the receiving process can be dynamically changed. Therefore, a receiving control unit 32 is provided in the control module 3. When the flexible probe 1 receives the returned ultrasonic signal, the ultrasonic signal received by each group of the probe array 11 is processed sequentially according to the relative deflection angles, so that time delay compensation for the ultrasonic signal is achieved, and focus problem confronted by the flexible probe 1 during the receiving process can be solved, and finally, an ultrasonic image is obtained.

By adopting this technical solution, the flexible probe can be used for ultrasound imaging, the application fields to which the flexible probe 1 applies increase, and it can partially replace rigid probes. In addition to that advantages, it can also simplify the operation steps for obtaining ultrasound images. Specifically, the operators only need to attach the flexible probe 1 to the surface of human body, then all of the probe units 111 can achieve the focus for the transmitting/receiving process. The operators do not have to pre-set the location, the shape, and the angle of the flexible probe, and they also do not have to control the flexible probe to move around, but a complete ultrasound image can also be obtained. For example, in the field of medical applications, when it is desired to perform ultrasound imaging detection on the patient's elbow joint, what the operators need to do is only to hold the flexible probe 1 in the hand, and to attach the flexible probe 1 to the elbow joint, so that an ultrasound image for the elbow joint can be obtained.

Figure 2:
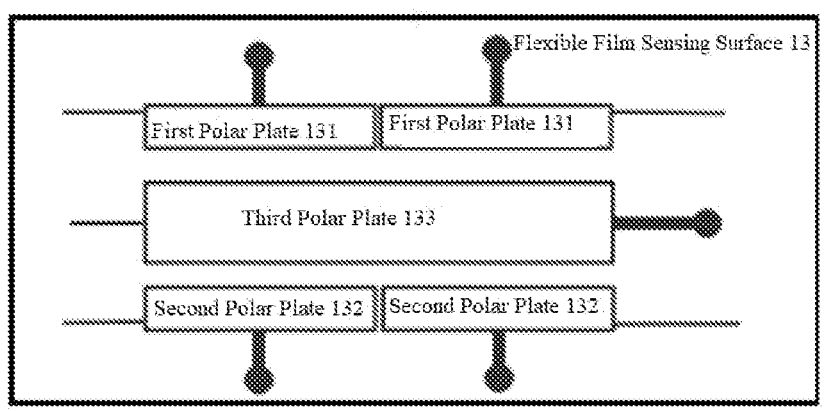
FIG. 2 is a schematic diagram of a flexible film sensor according to a preferred embodiment of the present invention.

In a preferred embodiment of the present invention, as shown in FIG. 2, the capacitive sensing array comprises:

a plurality of first polar plates 131;

a plurality of second polar plates 132, parallel to the plurality of first polar plates 131;

a plurality of third polar plates 133, disposed between the plurality of first polar plates 131 and the plurality of second polar plates 132, and connected to the flexible detection surface 12, wherein a first capacitance value is set between the plurality of third polar plates 133 and the plurality of first polar plates 131, a second capacitance value is set between the plurality of third polar plates 133 and the plurality of second polar plates 132;

a first initial standard value is set correspondingly to the first capacitance value;

a second initial standard value is set correspondingly to the second capacitance value;

a detection element, wherein the detection element is connected to the first polar plate 131, the second polar plate 132 and the third polar plate 133, respectively for obtaining a first difference value between the first capacitance value and the first initial standard value, and for obtaining a second difference value between the second capacitance value and the second initial standard value, and for obtaining the relative deflection angle of each of the plurality of probe units in the probe array based on the first difference value and the second difference value.

Specifically, a capacitance sensing array is arranged in the flexible film sensing surface 13, and a plurality of first electrode plates 131, a plurality of second electrode plates 132, and a plurality of third electrode plates 133 are arranged in the capacitance sensor array. When the operator attaches the flexible probe 1 to the human body, the flexible film sensing surface 13 will deform along the contour of the human body. The flexible detection surface 12 will also change with the deformation of the flexible film sensing surface 13. Therefore, both the first capacitance value and the second capacitance value change, and the first difference value and the second difference value may also change. The relative deflection angle of each of the probe units 111 in the probe array 11 in a corresponding row of probe unit 111 can be obtained according to the change of the first capacitance value and the second capacitance value, and the location of the probe unit 111 in the probe array 11.

Furthermore, in a more preferred embodiment of the present invention, two first polar plates 131, two second polar plates 132, and one third polar plate 133 are provided. When the flexible probe 1 is attached to the surface of the human body, each probe unit 111 has two first difference values and two second difference values. The relative deflection angles of the probe units 111 can be obtained by analyzing the difference values and taking into consideration the position of the probe unit 11 in the probe array 11.

In a more preferred embodiment of the present invention, after the relative deflection angles of the probe units 111 are obtained, the delay time for each of the probe unit 111 can be obtained by calculation the following formula:

$$\tau_{(i,j)} = \frac{\Delta R_{(i,j)}}{c} \tag{1}$$

wherein $\tau_{(i,j)}$ represents delay time of the probe unit 111;

i represents the row serial number of the probe unit 111 in the probe array 11, j represents the column serial number of the probe unit 111 in the probe array 11;

$\Delta R_{(i,j)}$ represents a sound path between the probe unit 111 and a preset focus; and c represents sound velocity.

In a more preferred embodiment of the present invention, the sound path between the probe unit 111 and the preset focus is expressed as:

$$\Delta R_{(i,j)} = [4r_{(i,j)}(r_{(i,j)}+F)\sin(\beta_{(i,j)}/2)+F^2]^{1/2} - F \tag{2}$$

wherein $r_{(i,j)}$ represents spatial distance between the probe unit 111 and a preset coordinate origin;

F represents the depth of the preset focus;

$\beta_{(i,j)}$ represents the deflection angle between the probe unit 11 and the preset coordinate origin.

Specifically, after the transmitting control unit 31 obtains the relative deflection angles of the probe unit 111, the first probe unit 11 in each row in the probe array 11 can, by combining formula (2), be adopted as the coordinate origin, to establish a corresponding spatial coordinate system. In this way, the sound path between the probe unit 111 and the preset focus is calculated, and then the transmitting control unit 31 obtains, by combining formula (1), the delay times corresponding to each probe unit 111.

In conclusion, the relative deflection angles of the flexible probe 1 in the ultrasound scanning can be obtained through the flexible film sensing unit 13, and the delay time of each probe unit 111 can be obtained through the relative deflection angles. The delay time is then considered as a transmission parameter to control the transmitting sequence of each of the probe units 111, so that transmission focus problem confronted by the flexible probe 1 during the ultrasound imaging process can be solved.

In a preferred embodiment of the present invention, the receiving control unit 32 comprises:

a beamforming element 321, connected to the flexible probe 1 and the switch module 2, respectively, configured to obtain the relative deflection angles, configured to control each row of probe units 111 in the probe array 11 to sequentially receive the ultrasonic signal through the switch module 2, and configured to perform beamforming on the ultrasonic signal based on the relative deflection angle and output the ultrasonic signal;

a signal processing element 322, connected to the beamforming element 321, configured to receive the ultrasonic signal output by the beamforming element 321, and configured to filter and compress the ultrasonic signal and output the ultrasonic signal; and an image processing element 323, connected to the signal processing element 322, configured to receive the ultrasonic signal output by the signal processing element 322, and configured to perform frame-related processing on the ultrasonic signal to generate the ultrasonic image.

Figure 3:
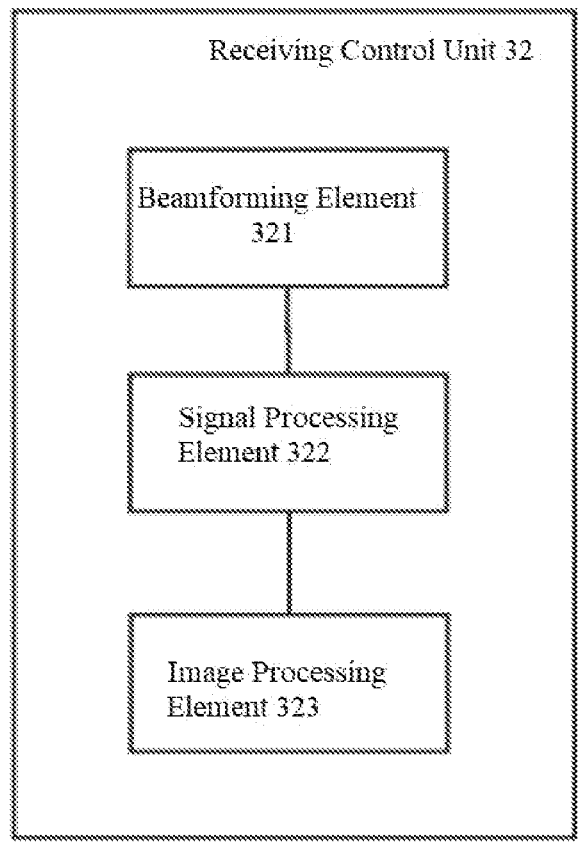
FIG. 3 is a schematic diagram of a transmitting control unit according to a preferred embodiment of the present invention.

Specifically, as shown in FIG. 3, the beamforming element 321 performs beamforming on the ultrasonic signal received by the probe units 111 based on the relative deflection angles. The signal processing element performs dynamic filtering, logarithmic compression, and demodulation on the ultrasonic signal. Accordingly, the ultrasonic signal is affected by noise generated during the sampling process and analog-to-electrical conversion of the ultrasound signals, then the image is not smooth enough. Therefore, the image processing element 323 performs frame-related processing and noise suppression on the ultrasound signal, and the ultrasound image is obtained.

In a more preferred embodiment of the present invention, wherein the coordinate origin is configured as one probe unit, which has a shortest sound path from the receiving focus thereto, in each row of plurality of probe units in the probe array, the beamforming element 321 is subjected to beamforming process by using the following formula:

$$S_{DAS}(t) = \sum_{i=0,j=0}^{i=n-1,j=m-1} s(t_{(i,j)} - t' - \tau_{(i,j)}) \tag{3}$$

wherein $S_{DAS}(t)$ represents the ultrasonic signal which is subjected to the beamforming process;

$s(t_{(i,j)})$ represents the ultrasonic signal received by the probe unit 111;

i represents a row serial number of the probe unit 111 in the probe array 11, n represents the number of rows in the probe array 11;

j represents a column serial number of the probe unit 111 in the probe array 11, m represents the number of columns in the probe array 11;

t' represents a transmission time of ultrasonic signal which indicates a shortest distance among distances between all of the plurality of probe units and the receiving focus;

$\tau_{(i,j)}$ represents the delay time of the one of plurality of probe units 111 relative to the coordinate origin.

Specifically, after each row of the probe units 11l in the probe array 11 transmit ultrasonic signal, the probe units 11 in the row start to receive the returned ultrasonic signal. After all the probe units 111 in the row have received the returned ultrasonic signal, next row of probe units 111 begin to transmit and receive the ultrasonic signal. It shows that data finally processed by each row of the probe units 111 are related to the relative deflection angle. Therefore, when the receiving control unit 32 performs beamforming, and when the probe units 111 receive the ultrasonic signal and perform beamforming, it is necessary to carry out a geometrical operation, by using the formula (2), for the relative deflection angle and the positional information of each probe unit 111, then the ultrasonic signal subjected to the beamforming process is obtained.

In conclusion, the beamforming element 321 can obtain the delay time of each probe unit 111 based on the relative deflection angle of the flexible probe 1 in the ultrasound scanning. The delay time is then considered as a receiving parameter to control the receiving sequence of each of the probe units 111, so that the receiving compensation for the ultrasonic signal is achieved, and focus problem confronted by the flexible probe 1 during the receiving process can be solved.

Therefore, after solving the transmitting focusing problem and the receiving focusing problem, the flexible probe 1 can be applied in the field of ultrasonic scanning and imaging technology as a detection terminal for ultrasonic scanning, so that the problem of rigid probes in the prior art can be solved, in which the problems refer to a complex operation and imaging steps of the rigid probes when they are applied to the fields of the ultrasonic scanning and imaging technology.

In a more preferred embodiment of the present invention, the ultrasonic system of a contact type flexible conformal ultrasonic probe further comprises a client, wherein the client is connected to the receiving control unit 32 for obtaining the ultrasonic image and displaying the obtained ultrasonic image.

Specifically, in order to allow the operator to view the ultrasonic image for user interaction, a client is arranged in the ultrasonic system. The client can obtain the ultrasonic image and display the ultrasonic image.

An ultrasonic method for a contact type flexible conformal ultrasonic probe, applied to any one of the ultrasonic systems for generating an ultrasonic image, wherein the ultrasonic method comprises the process of a flexible probe 1 transmitting the ultrasonic signal;

the transmitting process comprises:

Step A1, the transmitting control unit 31 controls the plurality of probe units 111 in the probe array 11 to switch to the transmitting state through the switch module 31;

Step A2, the transmitting control unit 31 obtains the relative deflection angles of the plurality of probe units 111 in the probe array 11, and generates delay times according to the relative deflection angles; and Step A3, the transmitting control unit 31 controls the plurality of probe units 111 to transmit ultrasonic signal according to the delay times.

Figure 4:
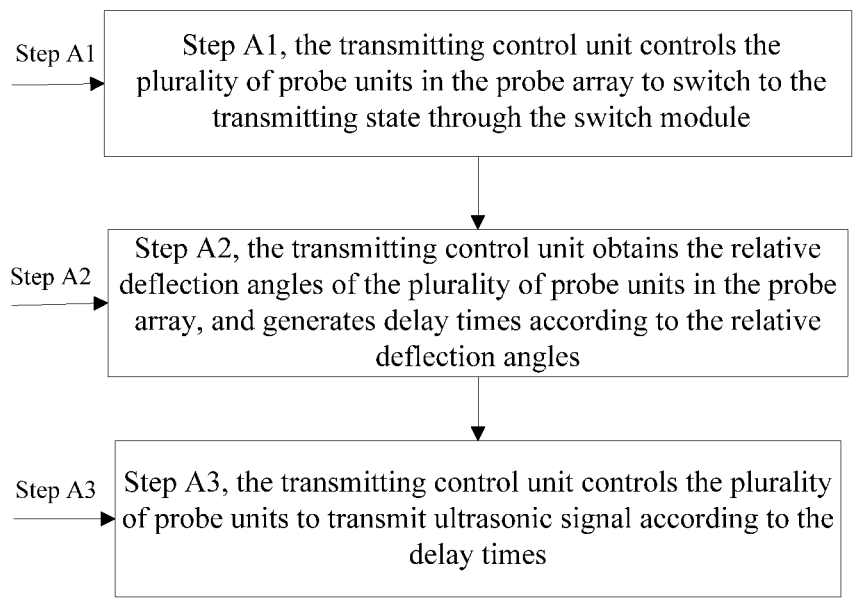
FIG. 4 is a schematic flowchart of a transmitting process according to a preferred embodiment of the present invention.

Specifically, as shown in FIG. 4, the flexible probe 1 comprises a probe array 11, and the probe array 11 comprises a plurality of probe units 111. When the probe units 111 transmit ultrasonic signal, in Step A1, the transmitting control unit 31 controls all the probe units 111 in the current row in the probe array 11 to be switched to the transmitting state, and then in Step A2, the transmitting control unit 31 obtains the relative deflection angles of all the probe units 111 in the current row, and generates the delay times corresponding to each probe unit 111 according to the respective relative deflection angles, so that all the probe units 111 in the current row can reach the focus at the same time in Step A3.

In a preferred embodiment of the present invention, the ultrasonic method further comprises the process of the flexible probe 1 receiving the ultrasonic signal;

the receiving process comprises:

Step B1, the receiving control unit 32 controls the plurality of probe units 111 in the probe array 11 to switch to the receiving state through the switch module 2;

Step B2, the receiving control unit 32 obtains the ultrasonic signal received by the probe units 111; and Step B3, the receiving control unit 32 obtains the relative deflection angles of the plurality of probe unit 111 in the probe array 11, and process the ultrasonic signal according to the relative deflection angle, so as to obtain an ultrasonic image.

Figure 5:
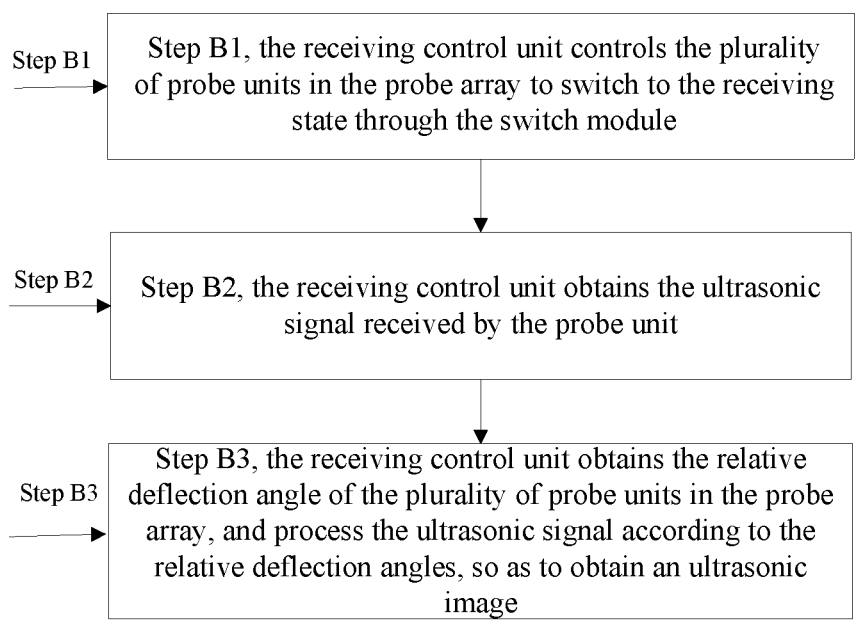
FIG. 5 is a schematic flowchart of a receiving process according a preferred embodiment of the present invention.

Specifically, as shown in FIG. 5, when the probe units 111 receive ultrasonic signal, in Step B1, the transmitting control unit 31 controls all the probe units 11I in the current row in the probe array 11 to be switched to the receiving state, and then in Step B2, the transmitting control unit 31 obtains the ultrasonic signal received by all the probe units 111 in the current row. As a result, the relative deflection angles of the probe units 111 in the probe array 11 can be obtained in Step B3, and the ultrasonic signal is processed according to the relative deflection angles, so that the ultrasound image is obtained.

In a preferred embodiment of the present invention, Step B3 further comprises:

Step B31: the beamforming element 321 in the receiving control unit 32 receives the ultrasonic signal, performs beamforming process on the ultrasonic signal based on the relative deflection angle, and outputs the ultrasonic signal;

Step B32: the signal processing element 322 in the receiving control unit 32 receives the ultrasonic signal output by the beamforming element 321, filters and compresses the ultrasonic signal, and outputs the ultrasonic signal; and Step B33: the image processing element 323 in the receiving control unit 32 receives the ultrasonic signal output by the signal processing element 322, and performs frame-related processing on the ultrasonic signal to generate the ultrasonic image.

Figure 6:
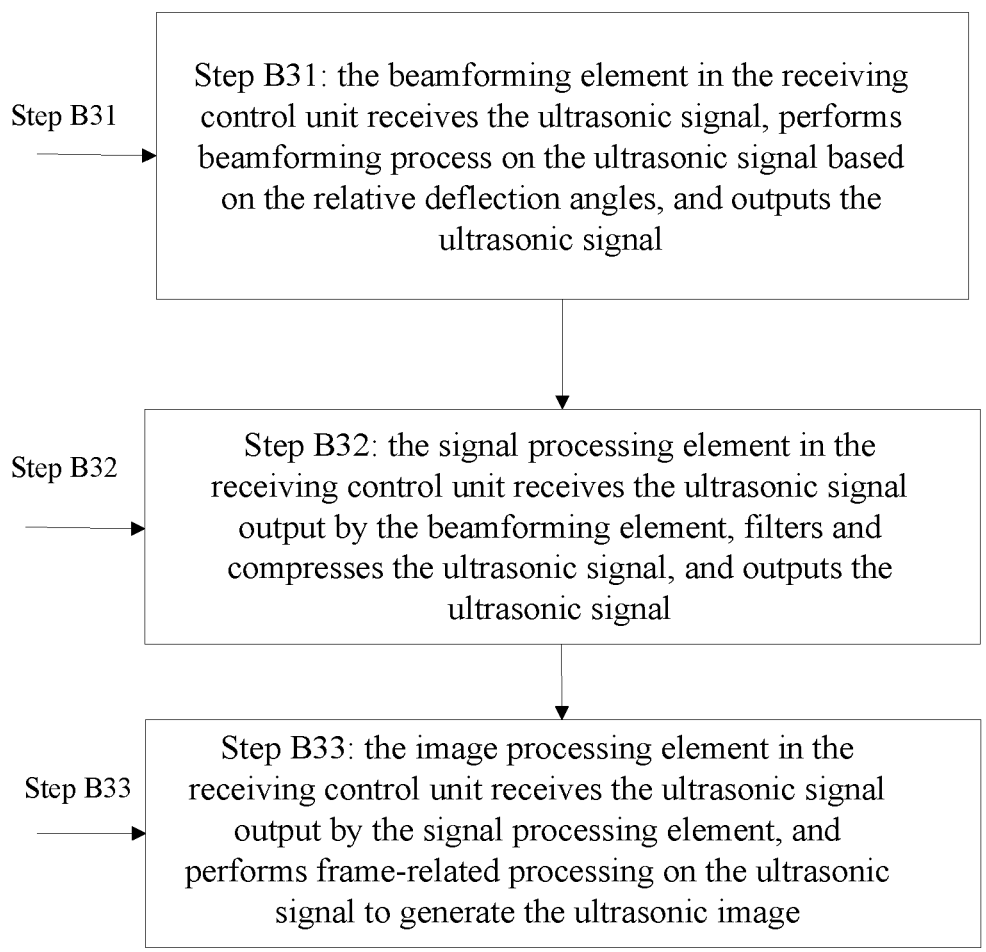
FIG. 6 is a schematic flowchart of Step B3 in a preferred embodiment of the present invention.

Specifically, as shown in FIG. 6, in Step B31, the beamforming element 321 performs beamforming process on the ultrasonic signal received by the probe unit 111 based on the relative deflection angle; in Step B32, the signal processing element performs dynamic filtering, logarithmic compression, demodulation, and dynamic processing on the ultrasonic signal; and in Step B33, the image processing element 323 may perform frame-related processing and noise suppression processing on the ultrasonic signal; finally, the ultrasonic image is generated.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. An ultrasonic system of a contact type flexible conformal ultrasonic probe for generating an ultrasonic image, comprising:
    a flexible probe, comprising a flexible detection surface, a plurality of probe units, and a soft film sensing surface, wherein the plurality of probe units are configured to transmit/receive an ultrasonic signal, all of the plurality of probe units form a probe array, the probe array is positioned inside the flexible detection surface, the flexible detection surface is connected to flexible film sensing surface and changes with deformation of the flexible film sensing surface, the flexible film sensing surface is provided with a capacitive sensor array therein, the capacitive sensor array is configured to detect the deformation of the flexible film sensing surface and to obtain relative deflection angles of each of the plurality of probe units in the probe array;
    a switch module, connected to the flexible probe, and configured to sequentially switch a transmitting/receiving state of each of the plurality of the probe units in the probe array;
    a control module, connected to the flexible probe and the switch module, respectively, the control module comprising:
    a transmitting control unit for acquiring the relative deflection angles of the plurality of probe units and generating corresponding delay time according to the relative deflection angles, and sequentially controlling the plurality of probe units in the probe array to transmit the ultrasonic signal according to the delay time; and
    a receiving control unit for sequentially controlling the plurality of probe units in the probe array to receive the ultrasonic signal, and for obtaining the relative deflection angles of plurality of probe units, and for performing beamforming and image processing on the ultrasonic signal, so as to obtain the ultrasonic image;
    the delay time for each of the probe unit is obtained by calculation the following formula $$\tau_{(i,j)} = \frac{\Delta R_{(i,j)}}{c} \quad (1)$$

wherein
    $\tau_{(i,j)}$ represents delay time of the probe unit;
    i represents a row serial number of the probe unit in the probe array, j represents a column serial number of the probe unit in the probe array;
    $\Delta R_{(i,j)}$ represents a sound path between the probe unit and a preset focus; and
    c represents sound velocity;
    the sound path between the probe unit and the preset focus is expressed as, $$\Delta R_{(i,j)} = [4r_{(i,j)}(r_{(i,j)}+F)\sin(\beta_{(i,j)}/2)+F^2]^{1/2} - F \quad (2)$$

wherein $r_{(i,j)}$ represents spatial distance between the probe unit and a preset coordinate origin;
    F represents depth of the preset focus;
    $\beta_{(i,j)}$ represents the deflection angle between the probe unit and the preset coordinate origin.

2. The ultrasonic system of a contact type flexible conformal ultrasonic probe of claim 1,
    wherein the capacitive sensing array comprises:
    a plurality of first polar plates;
    a plurality of second polar plates, parallel to the plurality of first polar plates;
    a plurality of third polar plates, disposed between the plurality of first polar plates and the plurality of second polar plates, and connected to the flexible detection surface, wherein a first capacitance value is set between the plurality of third polar plates and the plurality of first polar plates, a second capacitance value is set between the plurality of third polar plates and the plurality of second polar plates;
    a first initial standard value is set correspondingly to the first capacitance value;
    a second initial standard value is set correspondingly to the second capacitance value;
    a detection element, wherein the detection element is connected to the first polar plate, the second polar plate and the third polar plate, respectively, for obtaining a first difference value between the first capacitance value and the first initial standard value, and for obtaining a second difference value between the second capacitance value and the second initial standard value, and for obtaining the relative deflection angle of each of the plurality of probe units in the probe array relative to a corresponding coordinate origin based on the first difference value, the second difference value, and the position of each of the plurality of probe units in the probe array, wherein the coordinate origin is preset as one probe unit in a row of plurality of probe units in the probe array.

3. The ultrasonic system of a contact type flexible conformal ultrasonic probe of claim 2, wherein the receiving control unit comprises:
    a beamforming element, connected to the flexible probe and the switch module, respectively, configured to obtain the relative deflection angles of the plurality of probe units, configured to control each row of the plurality of probe units in the probe array to sequentially receive the ultrasonic signal through the switch module, and configured to perform beamforming on the ultrasonic signal based on the relative deflection angles and output the ultrasonic signal;
    a signal processing element, connected to the beamforming element, configured to receive the ultrasonic signal output by the beamforming element, and configured to filter and compress the ultrasonic signal and output the ultrasonic signal; and
    an image processing element, connected to the signal processing element, configured to receive the ultrasonic signal output by the image processing element, and configured to perform frame-related processing on the ultrasonic signal to generate the ultrasonic image.

4. The ultrasonic system of a contact type flexible conformal ultrasonic probe of claim 3, wherein the coordinate origin is configured as one probe unit, which has a shortest sound path from the receiving focus thereto, in each row of plurality of probe units in the probe array, wherein the beamforming element is subjected to beamforming process by using the following formula:

$$S_{DAS}(t) = \sum_{i=0, j=0}^{i=n-1, j=m-1} s(t_{(i,j)} - t' - \tau_{(i,j)})$$

wherein $S_{DAS}(t)$ represents the ultrasonic signal which is subjected to the beamforming process;

$s(t_{(i,j)})$ represents the ultrasonic signal received by one of the plurality of probe units;

i represents a row serial number of the one of the plurality of probe units in the probe array, n represents a number of rows of the plurality of probe units in the probe array;

j represents a column serial number of the one of the plurality of probe units in the probe array, m represents a number of columns of the plurality of probe units in the probe array;

t' represents a transmission time of ultrasonic signal which indicates a shortest distance among distances between all of the plurality of probe units and the receiving focus;

$\tau_{(i,j)}$ represents the delay time of the one of plurality of probe units relative to the coordinate origin.

5. The ultrasonic system of a contact type flexible conformal ultrasonic probe of claim 1, further comprising:

a client, wherein the client is connected to the receiving control unit for obtaining the ultrasonic image and displaying the ultrasonic image.

6. An ultrasonic method for a contact type flexible conformal ultrasonic probe, applied to the ultrasonic system of claim 1 for generating an ultrasonic image, wherein the ultrasonic method comprises the process of a flexible probe transmitting the ultrasonic signal;

the transmitting process comprises:

Step A1, the transmitting control unit controls the plurality of probe units in the probe array to switch to the transmitting state through the switch module;

Step A2, the transmitting control unit obtains the relative deflection angles of the plurality of probe units in the probe array, and generates delay times according to the relative deflection angles; and Step A3, the transmitting control unit controls the plurality of probe units to transmit ultrasonic signal according to the delay times.

7. The ultrasonic method for a contact type flexible conformal ultrasonic probe of claim 6, wherein the ultrasonic method further comprises the process of the flexible probe receiving the ultrasonic signal;

the receiving process comprises:

Step B1, the receiving control unit controls the plurality of probe units in the probe array to switch to the receiving state through the switch module;

Step B2, the receiving control unit obtains the ultrasonic signal received by the probe unit; and Step B3, the receiving control unit obtains the relative deflection angles of the plurality of probe units in the probe array, and process the ultrasonic signal according to the relative deflection angles, so as to obtain an ultrasonic image.

8. The ultrasonic method for a contact type flexible conformal ultrasonic probe of claim 7, wherein Step B3 further comprises:

Step B31: the beamforming element in the receiving control unit receives the ultrasonic signal, performs beamforming process on the ultrasonic signal based on the relative deflection angles, and outputs the ultrasonic signal;

Step B32: the signal processing element in the receiving control unit receives the ultrasonic signal output by the beamforming element, filters and compresses the ultrasonic signal, and outputs the ultrasonic signal;

Step B33: the image processing element in the receiving control unit receives the ultrasonic signal output by the signal processing element, and performs frame-related processing on the ultrasonic signal to generate the ultrasonic image.

9. The ultrasonic method of a contact type flexible conformal ultrasonic probe of claim 8, wherein the coordinate origin is configured as one probe unit, which has a shortest sound path from the receiving focus thereto, in each row of the plurality of probe units in the probe array, the beamforming element is subjected to beamforming process by using the following formula:

$$S_{DAS}(t) = \sum_{i=0, j=0}^{i=n-1, j=m-1} s(t_{(i,j)} - t' - \tau_{(i,j)})$$

wherein $S_{DAS}(t)$ represents the ultrasonic signal which is subjected to the beamforming process;

$s(t_{(i,j)})$ represents the ultrasonic signal received by the one of the plurality of probe units;

i represents the row serial number of the one of the plurality of probe units in the probe array, n represents the number of rows of the plurality of probe units in the probe array;

j represents the column serial number of the plurality of probe units in the probe array, m represents the number of columns of the plurality of probe units in the probe array;

t' represents the transmission time of the ultrasonic signal which indicates a shortest distance among distances between all of the plurality of probe units and the receiving focus;

$\tau_{(i,j)}$ represents the delay time of the one of the plurality of probe unit relative to the coordinate origin.

* * * * *